(12) United States Patent
Iwasaki et al.

(10) Patent No.: US 11,391,722 B2
(45) Date of Patent: Jul. 19, 2022

(54) DISPENSING APPARATUS AND DISPENSING METHOD

(71) Applicants: KAWASAKI JUKOGYO KABUSHIKI KAISHA, Kobe (JP); SYSMEX CORPORATION, Kobe (JP); MEDICAROID CORPORATION, Kobe (JP)

(72) Inventors: Yukio Iwasaki, Kobe (JP); Satoshi Ouchi, Kobe (JP); Eiji Mitsui, Kobe (JP); Junichi Matsuoka, Kobe (JP); Takehiro Hasegawa, Kobe (JP); Yukihiko Kitano, Kobe (JP)

(73) Assignees: KAWASAKI JUKOGYO KABUSHIKI KAISHA, Kobe (JP); SYSMEX CORPORATION, Kobe (JP)

( * ) Notice: Subject to any disclaimer, the term of this patent is extended or adjusted under 35 U.S.C. 154(b) by 0 days.

(21) Appl. No.: 16/226,704

(22) Filed: Dec. 20, 2018

(65) Prior Publication Data
US 2019/0195857 A1     Jun. 27, 2019

(30) Foreign Application Priority Data
Dec. 26, 2017 (JP) .............................. JP2017-250248

(51) Int. Cl.
*G01N 33/487* (2006.01)
*G01N 21/94* (2006.01)
(Continued)

(52) U.S. Cl.
CPC ....... *G01N 33/48778* (2013.01); *G01N 21/90* (2013.01); *G01N 21/94* (2013.01); *G01N 33/49* (2013.01)

(58) Field of Classification Search
CPC .. G01N 33/48778; G01N 21/94; G01N 21/90; G01N 21/51; G01N 21/64;
(Continued)

(56) References Cited

U.S. PATENT DOCUMENTS 4,083,637 A * 4/1978 Ellinger .................... B08B 9/46
                                                        250/223 B
4,240,751 A * 12/1980 Linnecke .............. B01L 3/5085
                                                        250/227.11
(Continued)

FOREIGN PATENT DOCUMENTS

JP    H07-260797 A    10/1995
JP    H09-218165 A    8/1997
(Continued)

OTHER PUBLICATIONS

Office Action (JPOA) dated Nov. 16, 2021 in a counterpart Japanese patent application.

*Primary Examiner* — Hoa Q Pham
(74) *Attorney, Agent, or Firm* — Metrolex IP Law Group, PLLC (57) ABSTRACT

A dispensing apparatus that dispenses a sample into a well of a microplate, including a light emitter that emits light to the well, a light receiver that receives light emitted by the light emitter and returned from the well; and a control unit that determines whether foreign matter is present in the well based on information on the light received by the light receiver.

7 Claims, 9 Drawing Sheets

(51) Int. Cl.
*G01N 21/90* (2006.01)
*G01N 33/49* (2006.01)

(58) Field of Classification Search
CPC ........ G01N 33/49; G01N 21/63; G01N 21/62; G01N 21/76; G01N 21/75; C12Q 1/6837; C12Q 1/6834; C12Q 1/6813; C12Q 1/68
USPC ..... 356/335–343, 73, 246; 506/7, 9; 436/91, 436/93, 94
See application file for complete search history.

(56) References Cited

U.S. PATENT DOCUMENTS

| | | | | |
|---|---|---|---|---|
| 6,864,985 | B1* | 3/2005 | Tanzer | G01N 21/51 356/337 |
| 7,173,270 | B1* | 2/2007 | Bruinsma | G01N 21/956 250/234 |
| 7,521,703 | B2* | 4/2009 | Nishigaki | G01N 21/253 250/577 |
| 9,575,060 | B2* | 2/2017 | Nishikawa | G01N 21/6486 |
| 2003/0036855 | A1* | 2/2003 | Harris | G02B 21/0064 702/19 |
| 2004/0051051 | A1* | 3/2004 | Kato | G01N 21/6452 250/458.1 |
| 2004/0259091 | A1* | 12/2004 | Yasuda | G01N 21/76 435/6.12 |
| 2006/0078998 | A1* | 4/2006 | Puskas | G01N 33/68 436/64 |
| 2008/0029690 | A1* | 2/2008 | Hashimoto | G01C 3/085 250/214.1 |
| 2008/0311677 | A1* | 12/2008 | Chin | G01N 33/54326 436/526 |
| 2014/0134608 | A1* | 5/2014 | Hanashi | G01N 21/6408 435/5 |
| 2015/0138552 | A1* | 5/2015 | Hirono | G01N 21/0332 356/337 |
| 2015/0212060 | A1* | 7/2015 | Van Mechelen | G01N 21/55 250/338.1 |
| 2015/0218628 | A1* | 8/2015 | Hanashi | G01N 21/65 506/9 |
| 2016/0231240 | A1* | 8/2016 | Battefeld | G01N 21/47 |
| 2016/0290931 | A1* | 10/2016 | Taike | G01N 21/51 |
| 2017/0205270 | A1* | 7/2017 | Luedemann | G01B 9/0209 |
| 2017/0309036 | A1* | 10/2017 | Perraut | G01N 21/453 |
| 2019/0178776 | A1* | 6/2019 | LeFevere | G01N 15/0625 |
| 2020/0319217 | A1* | 10/2020 | Verhoef | H04N 7/183 |

FOREIGN PATENT DOCUMENTS

| | | |
|---|---|---|
| JP | 2000-19184 A | 1/2000 |
| JP | 2003-149094 A | 5/2003 |
| JP | 2007-309888 A | 11/2007 |
| JP | 2009-103492 A | 5/2009 |
| JP | 2011-112501 A | 6/2011 |

* cited by examiner

DISPENSING APPARATUS AND DISPENSING METHOD

CROSS REFERENCE TO RELATED APPLICATIONS

This application claims priority based on 35 USC 119 from prior Japanese Patent Application No. 2017-250248 filed on Dec. 26, 2017, entitled "DISPENSING APPARATUS AND DISPENSING METHOD", the entire contents of which are incorporated herein by reference.

BACKGROUND

The disclosure relates to a dispensing apparatus and a dispensing method for detecting whether foreign matter is contained in a container holding a sample.

Heretofore, there have been disclosed methods of detecting, by using an optical scheme, whether foreign matter such as fibrin or a clot is contained in a sample held in a well in a microplate. One of such methods is disclosed in Japanese Patent Application Publication No. 2011-112501 ("Patent Literature 1"), for example. The method In Patent Literature 1 includes: capturing an image of a sample by a CCD camera; and detecting whether foreign matter such as fibrin or a clot is contained in the sample based on image information of the image captured.

In the method disclosed in Patent Literature 1, various parameters are obtained as image information from the image of the sample held in a well of a microplate. However, the method does not aim at detection of whether foreign matter such as fibrin is contained in wells of a microplate not holding a sample.

In view of the above circumstances, the disclosure has an object to provide a dispensing apparatus and a dispensing method that are capable of detecting whether foreign matter is contained in wells of a microplate.

SUMMARY

In accordance with one or more embodiments, a dispensing apparatus that dispenses a sample into a well of a microplate, and that includes: a light emitter that emits light to the well; a light receiver that receives light emitted by the light emitter and returned from the well; and a control unit that determines whether foreign matter is present in the well based on information on the light received by the light receiver.

In accordance with one or more embodiments, a dispensing method of dispensing a sample into a well in a microplate, the method including: emitting light to the well; determining whether foreign matter is present in the well; and dispensing the sample into the well

DETAILED DESCRIPTION

Embodiments are explained with referring to drawings. In the respective drawings referenced herein, the same constitutions are designated by the same reference numerals and duplicate explanation concerning the same constitutions is basically omitted. All of the drawings are provided to illustrate the respective examples only. No dimensional proportions in the drawings shall impose a restriction on the embodiments. For this reason, specific dimensions and the like should be interpreted with the following descriptions taken into consideration. In addition, the drawings include parts whose dimensional relationship and ratio are different from one drawing to another.

Hereinafter, a dispensing apparatus and a dispensing method according to one or more embodiments of the disclosure are described with reference to the accompanying drawings.

Figure 1:
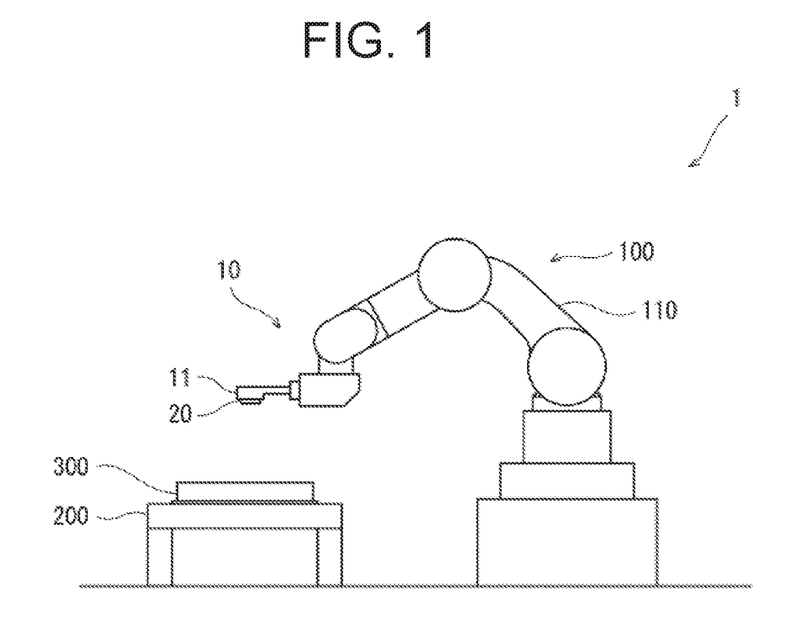
FIG. 1 is a diagram illustrating a side view of a foreign matter detecting apparatus according to one or more embodiments.

FIG. 1 is a side view illustrating a dispensing apparatus 1 according to one or more embodiments of the disclosure.

The dispensing apparatus 1 includes a main body 100 and a microplate placement table 200. A microplate 300 is placed on the microplate placement table 200. In the present embodiment, the main body 100 is used as an articulated industrial robot. The main body 100 used in one or more embodiments includes a robot arm 110. Then, the main body 100 includes a robot control unit 14.

The main body 100 includes a hand section 10. The hand section 10 includes two finger parts 11. The hand section 10 is configured to be capable of holding a foreign matter detecting unit 20 with the two finger parts 11.

The foreign matter detecting unit 20 is configured to be capable of measuring the distance from a detection target. In the present embodiment, the foreign matter detecting unit 20 includes a light emitter that emits light to the detection target, and a light receiver that receives light emitted by the light emitter. In the present embodiment, the light emitter emits light to a well. Then, the light receiver receives light emitted by the light emitter and returned from the well. If foreign matter is absent in the well, the light receiver receives light emitted by the light emitter and reflected by the well. If foreign matter is present in the well, the light receiver receives light emitted by the light emitter and reflected by the foreign matter. In either case, the light receiver receives light emitted to the well and returned from the well.

In the present embodiment, the foreign matter detecting unit 20 is a single unit in which the light emitter and the light receiver are incorporated and integrated. Further, in the present embodiment, light emitted by the light emitter is a laser beam.

The foreign matter detecting unit 20 emits a laser beam from the light emitter and receives the laser beam, reflected by the detection target, by the light receiver. Then, the foreign matter detecting unit 20 is capable of measuring the distance between the foreign matter detecting unit 20 and the detection target by detecting a phase difference between the laser beam emitted by the light emitter and the laser beam reflected by the detection target and received by the light receiver. In other words, the foreign matter detecting unit 20 functions as a distance sensor for measuring a distance. In the present embodiment, the foreign matter detecting unit 20 uses a laser beam as light emitted by the light emitter. Since the laser beam is light which tends not to scatter, the foreign matter detecting unit 20 is capable of efficiently emitting light to a sample in a well 310 to be subjected to detection. Therefore, the measurement of the distance by the foreign matter detecting unit 20 can be carried out easily.

Figure 2A:
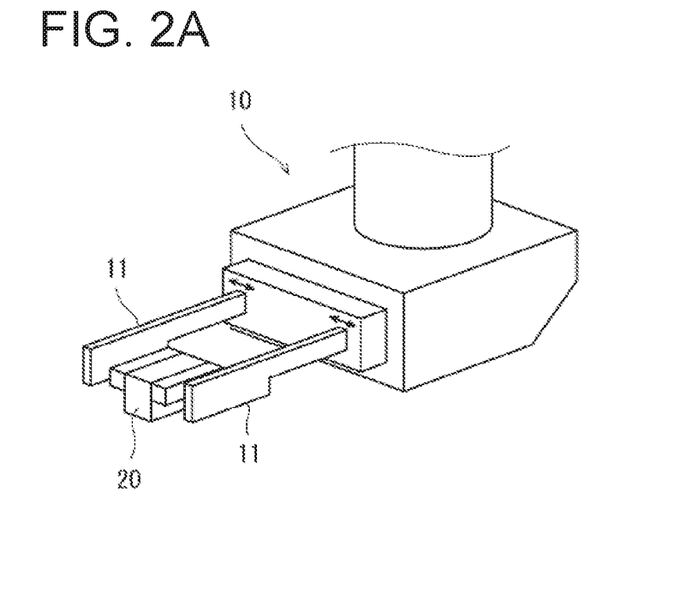
FIGS. 2A and 2B are diagrams illustrating perspective views of a hand section in a foreign matter detecting apparatus, such as in FIG. 1.
Figure 2B:
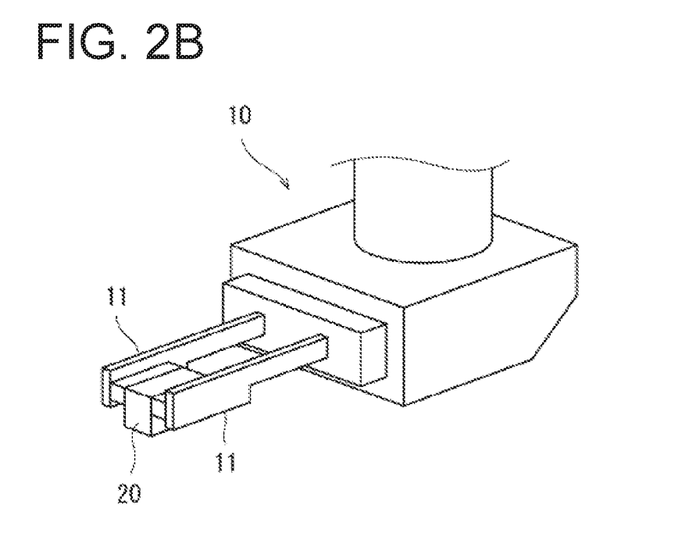

FIGS. 2A and 2B are enlarged perspective views of the hand section 10. As illustrated in FIG. 2A, the two finger parts 11 are configured to be movable in directions in which the finger parts 11 come close to and get away from each other.

FIG. 2A depicts a state where the two finger parts 11 are away from each other. Meanwhile, FIG. 2B depicts a state where the two finger parts 11 are close to each other, and pinch and hold the foreign matter detecting unit 20 in between. The foreign matter detecting unit 20 can be held by the two finger parts 11 by: placing the foreign matter detecting unit 20 between the two finger parts 11 at positions away from each other; and moving the two finger parts 11 from the above positions toward each other to bring the finger parts 11 into contact with the foreign matter detecting unit 20.

Figure 3:
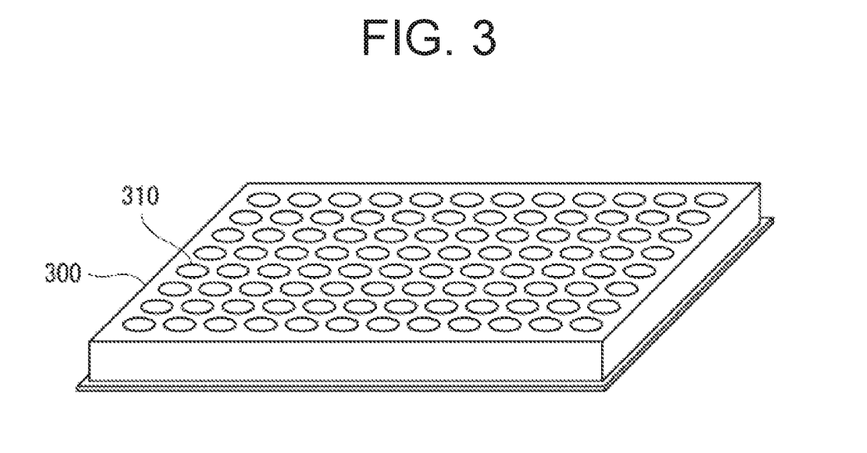
FIG. 3 is a diagram illustrating a perspective view of a microplate on which whether foreign matter is present is determined by a foreign matter detecting apparatus, such as in FIG. 1.

FIG. 3 is a perspective view illustrating a microplate 300 used in the present embodiment. The microplate 300 is a plate mainly used for purposes such as biochemical analysis and clinical examination. The microplate 300 is formed of a transparent resin is formed of polyethylene, polypropylene, or the like, for example. In the microplate 300, wells (sample containers) 310 are formed as holes each capable of holding liquid such as a sample. In the present embodiment, totally 96 wells 310 are formed with twelve wells arranged in a longitudinal direction and eight wells arranged in a short-side direction. In general, a sample is injected into a well 310 in the microplate 300 and an analysis or test is performed on the sample.

In the present embodiment, blood is injected as a sample into the well 310 of the microplate 300. A minute groove is formed on a bottom surface of the well 310. When the blood is injected into the well 310, the blood enters the inside of the groove 320 on the bottom surface of the well 310 shown in FIG. 5. After completion of the injection of the blood into the well 310, the inside of the well 310 is washed. After the inside of the well 310 is washed, only the blood stored in the groove 320 remains out of the blood injected into the well 310. Then, an analysis or test on the blood remaining in the groove 320 is performed in a later step.

In the present embodiment, the dispensing apparatus 1 includes a dispenser, not illustrated, which dispenses samples into the wells 310 of the microplate 300 as described above. The dispenser may be configured of a pipette attached to the hand of the main body 100. In other words, the dispensing apparatus 1 may be configured to dispense samples into the wells of the microplate 300 by means of the pipette attached to the hand of the main body 100.

Figure 4A:
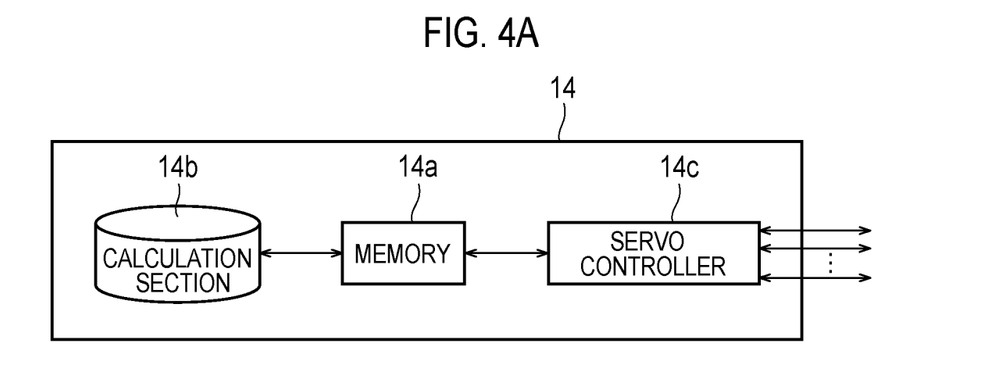
FIG. 4A is a block diagram illustrating a configuration of a control system for a main body in a foreign matter detecting apparatus, such as in FIG. 1.

Next, a control configuration of the main body 100 is explained. FIG. 4A is a block diagram of the control configuration of the main body 100.

As illustrated in FIG. 4A, the robot control unit 14 in the main body 100 includes a calculation section 14a, a memory 14b, and a servo controller 14c.

The robot control unit 14 is a robot controller including a computer, such as a micro controller, for example. Here, the robot control unit 14 may be configured of a single robot control unit 14 which performs centralized control, or of two or more robot control units 14 which perform distributed control in collaboration with each other.

The memory 14b stores therein information such as a basic program for the robot controller and various kinds of fixed data. The calculation section 14a controls various operations of the main body 100 by loading software such as the basic program stored in the memory 14b and executing the loaded software. More specifically, the calculation section 14a generates control commands for the main body 100, and outputs the control commands to the servo controller 14c. For example, the calculation section 14a can be configured of a processor unit.

The servo controller 14c is configured to control the driving of servo motors corresponding to respective joints of the robot arm 110 in the main body 100 based on each control command generated by the calculation section 14a.

Figure 4B:
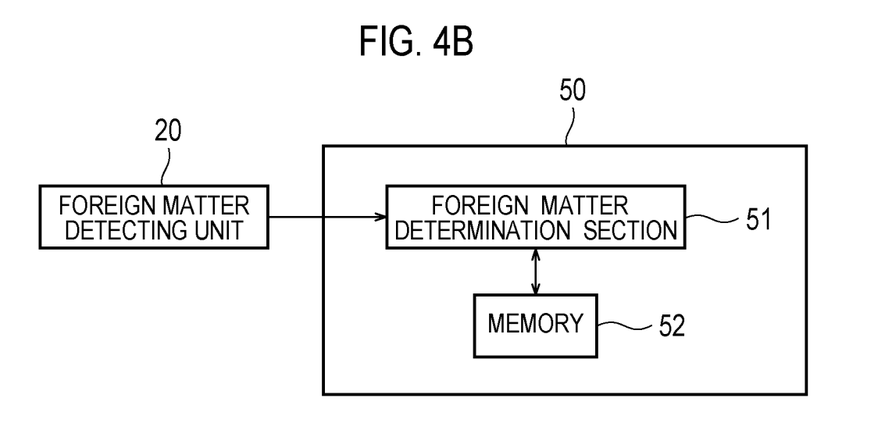
FIG. 4B is a block diagram illustrating a configuration of a control system for detection of foreign matter by a foreign matter detecting apparatus, such as in FIG. 1.

FIG. 4B is a block diagram of a configuration of a control system for the dispensing apparatus 1 to detect foreign matter.

As illustrated in FIG. 4B, the dispensing apparatus 1 includes a foreign matter detection control unit (control unit) 50 as a control unit for a mechanism that detects foreign matter. The foreign matter detection control unit 50 determines whether foreign matter is present in a well based on optical information of light received by the light receiver. The foreign matter detection control unit 50 includes a foreign matter determination section 51 and a memory 52.

The foreign matter determination section 51 can determine whether foreign matter is present in a well 301 of the microplate 300 based on a distance measured by the foreign matter detecting unit 20. The memory 52 stores therein data such as a threshold for the distance measured by the foreign matter detecting unit 20. The foreign matter determination section 51 reads the threshold for the distance stored in the memory 52, and determines whether foreign matter is present in the well 301 by comparing the distance measured by the foreign matter detecting unit 20 with the threshold for the distance.

Next, description is provided for detection that the dispensing apparatus 1 in the present embodiment performs to determine whether foreign matter is present in a well 310 to be subjected to detection in the microplate 300.

Figure 5:
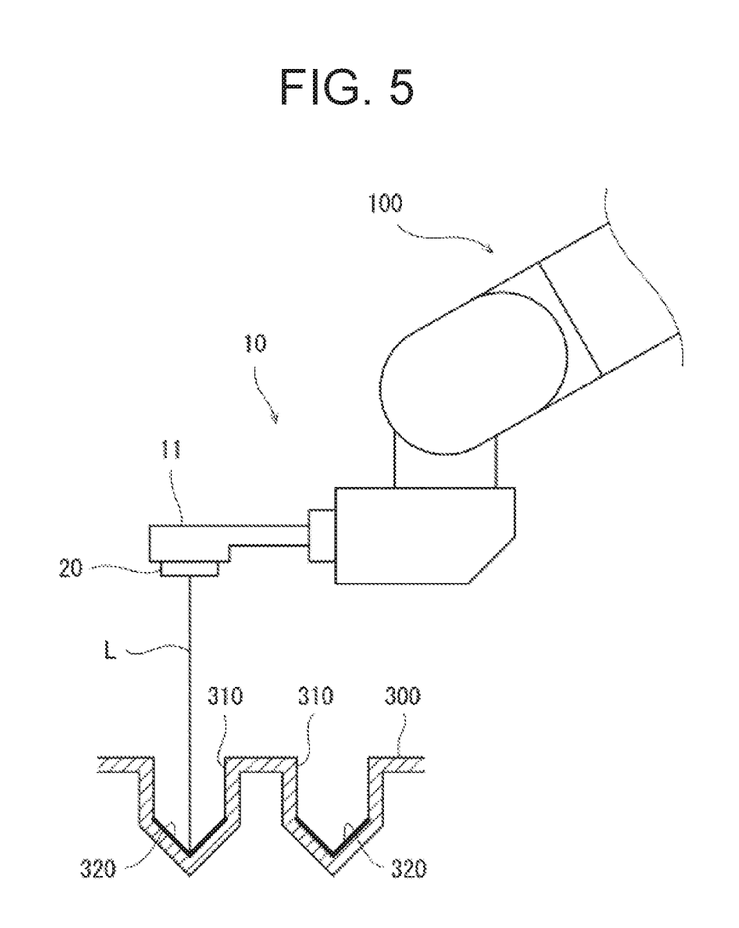
FIG. 5 is a structural diagram illustrating a foreign matter detecting apparatus, such as in FIG. 1, and a microplate in a state where the foreign matter detecting apparatus detects whether foreign matter is present in a well to be subjected to detection in a situation where foreign matter is absent in the well to be subjected to detection.

FIG. 5 is a structural diagram of the main body 100 in the dispensing apparatus 1 and the microplate 300 during detection of whether foreign matter is present in a well 310 to be subjected to detection in the microplate 300. FIG. 5 is the structural diagram of the main body 100 in the dispensing apparatus 1 and the microplate 300 during detection of whether foreign matter is present in the well 310 in a situation where foreign matter is absent in the well 310 to be subjected to detection. At the time of the detection of whether the foreign matter is present, the blood in the wells 310 is already removed by washing, and the blood remains only inside the groove 320.

In detecting whether foreign matter is present in a well 310 to be subjected to detection in the microplate 300, the light emitter in the foreign matter detecting unit 20 emits a laser beam. The foreign matter detecting unit 20 emits the laser beam to the inside of a well 310 to be subjected to detection. Thus, the laser beam emitted from the light emitter in the foreign matter detecting unit 20 travels inside the well 310.

In the situation illustrated in FIG. 5, foreign matter is absent in the well 310 to be subjected to detection, and therefore the laser beam emitted from the light emitter in the foreign matter detecting unit 20 can reach the liquid surface of the blood stored inside the groove 320 on the bottom surface of the well 310 to be subjected to detection.

After completion of the operation of injecting the blood into the wells 310 and washing the insides of the wells 310, the foreign matter detecting unit 20 measures the distance to the blood stored in the groove 320 on the bottom surface of each well 310 to be subjected to detection. In this process, the distance from the foreign matter detecting unit 20 to the liquid surface of the blood in the groove 320 on the bottom surface of the well 310 is detected based on a phase difference between the laser beam emitted from the light emitter and the laser beam reflected by the liquid surface of the blood and received by the light receiver.

In the situation in FIG. 5, since foreign matter is absent in the well 310, the distance between the foreign matter detecting unit 20 and the liquid surface of the blood in the groove 320 on the bottom surface of the well 310 is outputted as a result of the operation in which the foreign matter detecting unit 20 measures the distance from the foreign matter detecting unit 20 to the sample in the well 310. If a normal distance is outputted as the distance between the foreign matter detecting unit 20 and the liquid surface of the blood in the groove 320 on the bottom surface of the well 310, it is determined that anything that blocks the light axis L of the laser beam is not present in the well 310 to be subjected to detection and therefore foreign matter is absent therein. In this way, the absence of the foreign matter is detected in the well 310 to be subjected to detection.

Figure 6:
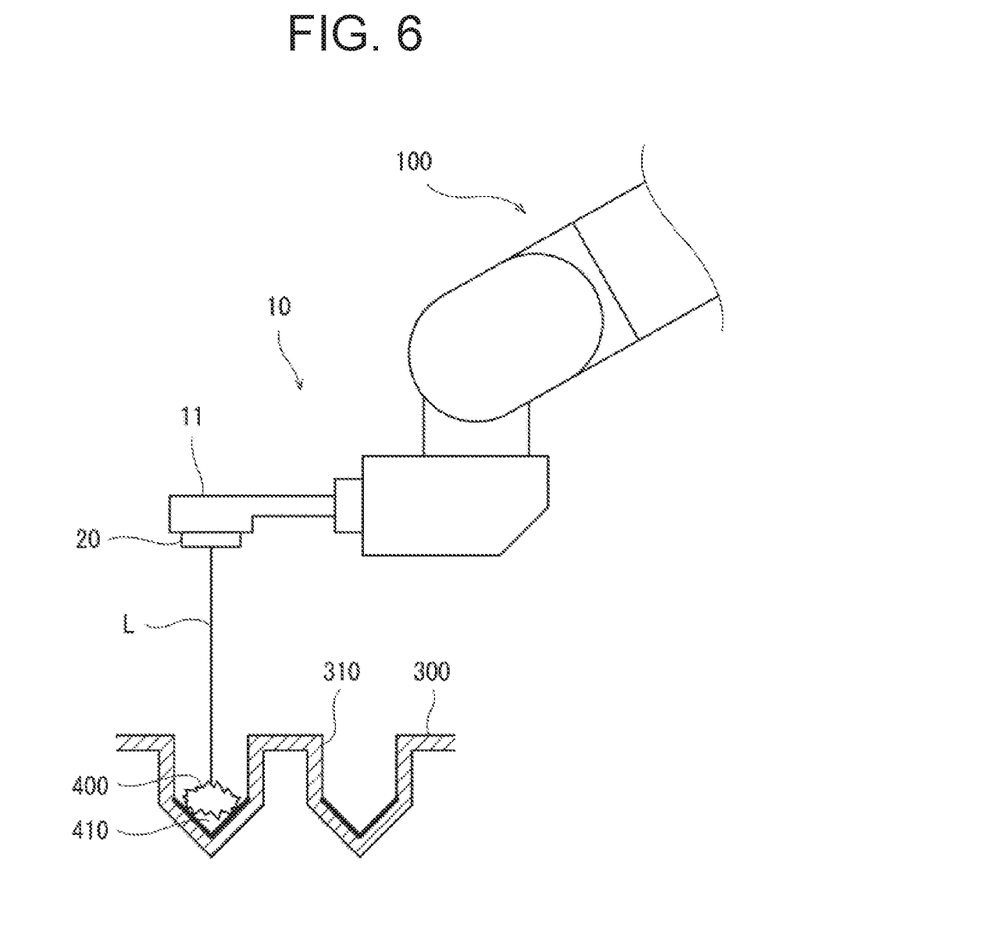
FIG. 6 is a structural diagram illustrating a foreign matter detecting apparatus, such as in FIG. 1, and a microplate in a state where the foreign matter detecting apparatus detects whether foreign matter is present in a well to be subjected to detection in a situation where foreign matter is present in the well to be subjected to detection.

FIG. 6 is a structural diagram of the main body 100 in the dispensing apparatus 1 and the microplate 300 during detection of whether foreign matter is present in a situation where foreign matter 400 is present in a well 310 to be subjected to detection.

In the situation illustrated in FIG. 6, the foreign matter 400 is present at the entrance of the well 310 to be subjected to detection, and blocks the light axis L of the laser beam emitted from the light emitter in the foreign matter detecting unit 20. Since the foreign matter 400 occludes a part of the well 310, the inside of the well 310 is not completely washed in the washing step, and therefore blood 410 of a sample remains inside the well 310. Examples of the foreign matter 400 include fibrin in the blood, a clot formed by blood coagulation, and the like.

When the foreign matter 400 is present in the well 310 to be subjected to detection, the light axis L of the laser beam emitted from the light emitter is blocked by the foreign matter in the process where the foreign matter detecting unit 20 detects the distance to the sample inside the well 310. Thus, the laser beam emitted by the light emitter is reflected by the foreign matter 400 in the middle of the light path without reaching the bottom surface of the well 310 and then turns back to the light receiver. In this case, a distance shorter than the distance between the foreign matter detecting unit 20 and the liquid surface of the blood in the groove 320 on the bottom surface of the well 310 is outputted as the distanced from the foreign matter detecting unit 20 to the sample.

For this reason, when the distance shorter than the distance between the foreign matter detecting unit 20 and the sample to be outputted in the case where the foreign matter 400 is absent in the well 310 is outputted as the distance from the foreign matter detecting unit 20 to the sample, it is determined that the foreign matter is present in the well 310. In this way, the presence of the foreign matter is detected in the well 310 to be subjected to detection. This detection process may employ a method including: setting a threshold for a detected distance; and determining the presence of foreign matter in the well 310 to be subjected to detection if the distance to the liquid surface of the blood in the well 310 detected by the foreign matter detecting unit 20 is smaller (shorter) than the threshold.

In the present embodiment, whether foreign matter is present in a well 310 to be subjected to detection is determined by the foreign matter determination section 51 in the foreign matter detection control unit 50 based on the distance measured by the foreign matter detecting unit 20. A personal computer (PC), for example, located separately from the main body 100 may perform a role of the foreign matter detection control unit 50. In this case, a CPU mounted inside the PC may function as the foreign matter detection control unit 50. In this manner, the foreign matter determination section 51 in the foreign matter detection control unit 50 inside the PC may determine whether foreign matter is present based on the distance measured by the foreign matter detecting unit 20.

Moreover, the robot control unit 14 may be configured to have the function as the foreign matter detection control unit 50. The robot control unit 14 may include the foreign matter detection control unit 50, and the foreign matter detection control unit 50 may determine whether foreign matter is present based on the distance measured by the foreign matter detecting unit 20.

The foreign matter detection control unit 50 and the robot control unit 14 may be configured of the same control unit or be configured of different control units.

Next, description is provided for a flow in which the dispensing apparatus 1 detects whether foreign matter is present in wells 310 to be subjected to detection in a microplate 300.

FIGS. 7A to 7D are structural diagrams illustrating steps in which the main body 100 in the dispensing apparatus 1 detects whether foreign matter is present. In addition, FIG. 8 is a flowchart presenting the flow in which the dispensing apparatus 1 detects whether foreign matter is present.

Figure 7A:
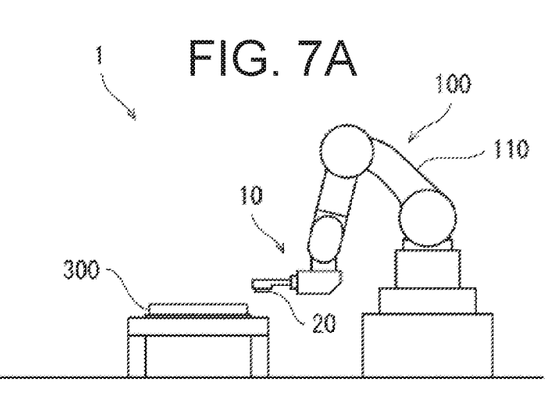
FIGS. 7A to 7D are structural diagrams illustrating a foreign matter detecting apparatus, such as in FIG. 1, a microplate, and their surroundings in steps where the foreign matter detecting apparatus detects whether foreign matter is present.
Figure 8:
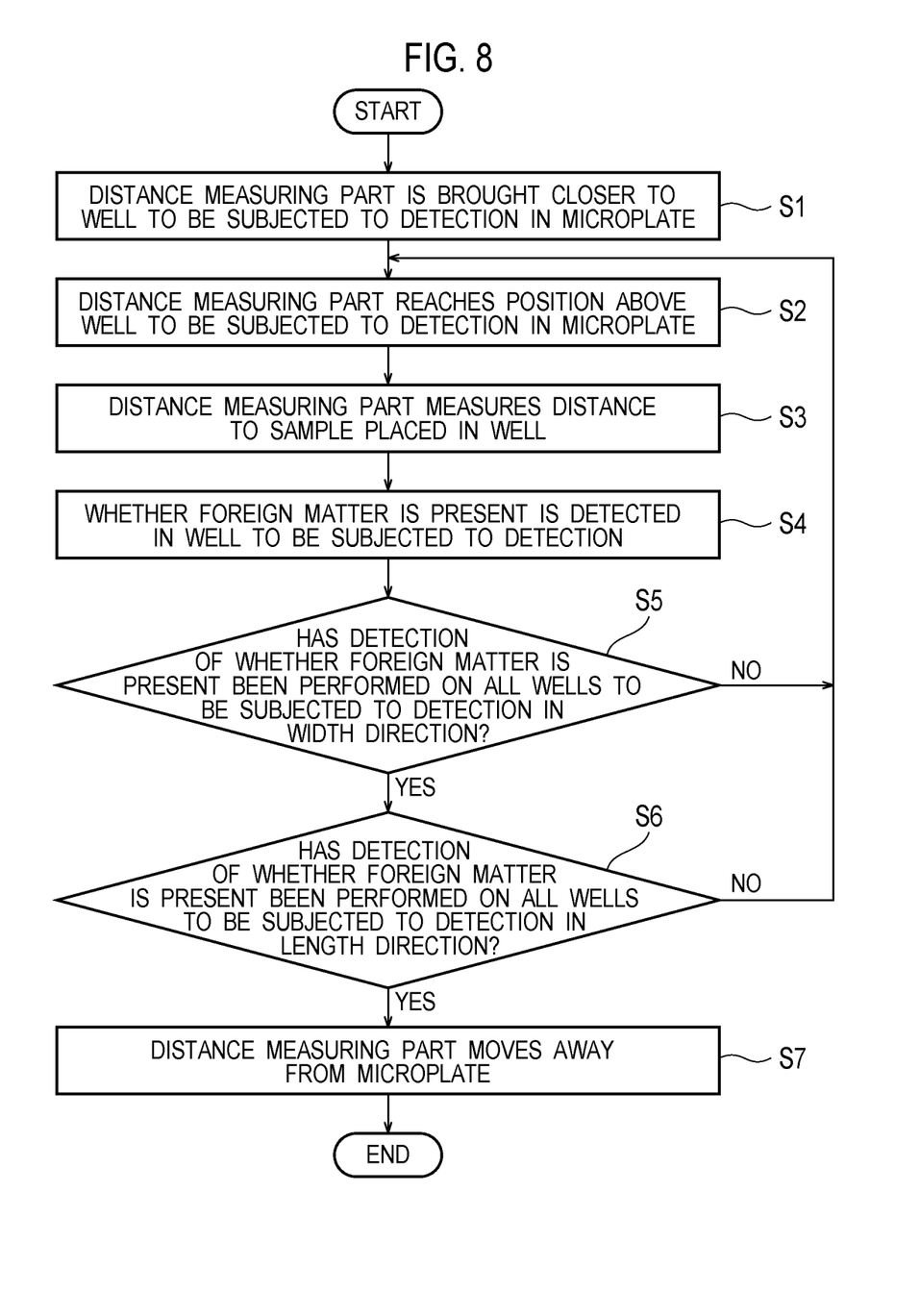
FIG. 8 is a flowchart illustrating a flow in which a foreign matter detecting apparatus, such as in FIG. 1, detects whether foreign matter is present.

A state illustrated in FIG. 7A is a state after the sample is dispensed into the wells 310 in the microplate 300 (dispensing step) and then the insides of the wells 310 are already washed. After the operation of injecting samples into the wells 310 and washing the insides of the wells 310, whether foreign matter is present is detected for each of the wells 310.

First, as illustrated in FIG. 7A, under control of the driving of the robot arm 110 in the main body 100 in the dispensing apparatus 1, the foreign matter detecting unit 20 in the hand section 10 is moved and brought closer to the microplate 300. In this way, the hand section 10 is moved to bring the foreign matter detecting unit 20 closer to the wells 310 to be subjected to detection in the microplate 300 (S1).

Figure 7B:
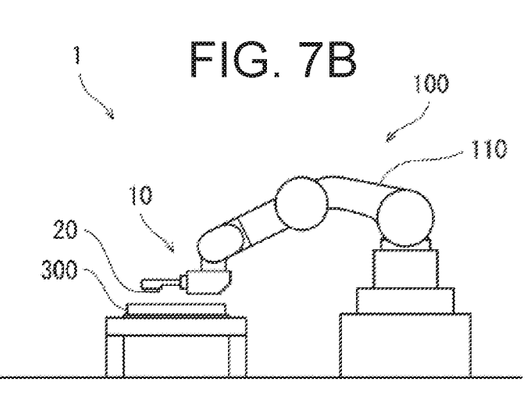

When the foreign matter detecting unit 20 reaches a position above a well 310 to be subjected to detection as illustrated in FIG. 7B (S2) as a result of moving the hand section 10 under the control of the driving of the robot arm 110, the light emitter at that position emits a laser beam (light emission step) from the foreign matter detecting unit 20 to the well 310 to be subjected to detection.

Figure 7C:
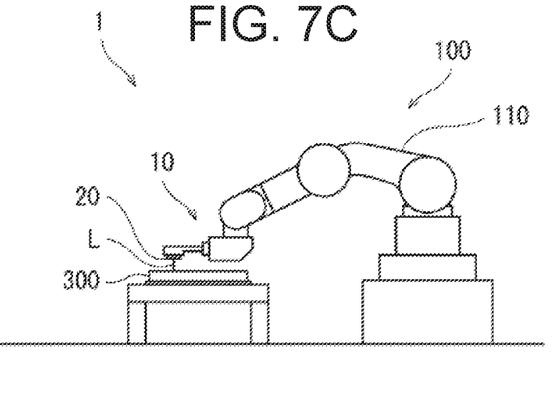

FIG. 7C illustrates a state where the light emitter emits a laser beam from the foreign matter detecting unit 20 to the well 310 to be subjected to detection. Thereby, the distance from the foreign matter detecting unit 20 to the liquid surface of the blood in the well 310 is detected (S3).

If the distance between the foreign matter detecting unit 20 and the liquid surface of the blood in the groove 320 on the bottom surface of the well 310 is outputted as a result of detecting the distance from the foreign matter detecting unit 20 to the liquid surface of the blood in the well 310, it is determined that foreign matter is absent in the well 310 to be subjected to detection. In this way, the absence of foreign matter in the well 310 to be subjected to detection is detected.

On the other hand, if a distance shorter than the distance between the foreign matter detecting unit 20 and the liquid surface of the blood in the groove 320 on the bottom surface of the well 310 is outputted as a result of detecting the distance from the foreign matter detecting unit 20 to the liquid surface of the blood in the well 310, it is determined that something blocking the light axis L is present in the well 310 to be subjected to detection and the foreign matter is present therein. In this way, the presence of foreign matter in the well 310 to be subjected to detection is detected.

As described above, the foreign matter detecting unit 20 measures the distance to the liquid surface of the blood detects, whereby whether foreign matter is present in the well 310 to be subjected to detection is determined and thus whether foreign matter is present in the well 310 is detected (S4) (determination step).

Upon completion of the detection of whether foreign matter is present in the wells 310 to be subjected to detection, a determination is made as to whether the detection of whether foreign matter is present has been performed on all the wells 310 to be subjected to detection in the width direction (S5).

If the detection of whether foreign matter is present has not been performed yet on all the wells 310 to be subjected to detection in the width direction, the flow returns to S2 and the detection of whether foreign matter is present is performed on the next well 310 to be subjected to detection. The steps S2 to S4 of detecting the presence or absence of forging matter are iterated until completion of the detection of whether foreign matter is present on all the wells 310 to be subjected to detection in the width direction.

If it is confirmed that the detection of whether foreign matter is present has been performed on all the wells 310 to be subjected to detection in the width direction, then a determination is made as to whether the detection of whether foreign matter is present has been performed on all the wells 310 to be subjected to detection in a length direction in the microplate 300 (S6).

If the detection of whether foreign matter is present has not been performed on all the wells 310 to be subjected to detection in the length direction, the flow returns to S2 and the detection of whether foreign matter is present is performed on the wells 310 in the next row to be subjected to detection. The steps S2 to S4 of detecting the presence or absence of forging matter are iterated until completion of the detection of whether foreign matter is present on the wells 310 in all the rows to be subjected to detection in the length direction and completion of the detection of whether foreign matter is present on all the wells 310 to be subjected to detection in the microplate 300.

Figure 9:
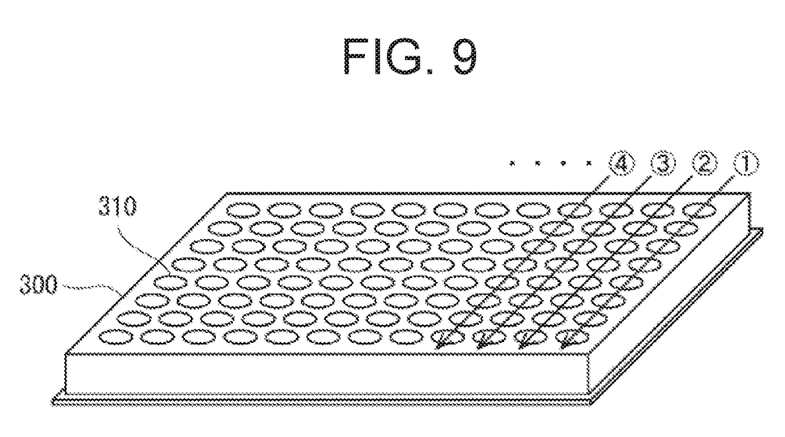
FIG. 9 is a structural diagram illustrating an order of wells in a microplate in the detection of whether foreign matter is present when a foreign matter detecting apparatus, such as in FIG. 1, detects whether foreign matter is present.

FIG. 9 is a structural diagram presenting an order of wells 310 in the microplate 300 in the detection of whether foreign matter is present.

First, the detection of whether foreign matter is present is performed on the wells 310 in a row (row 1) at one length-wise end of the microplate 300 in an order from one end to the other end of the row. Upon completion of the detection of whether foreign matter is present in all the wells 310 from the one end to the other end of the row, the foreign matter detecting unit 20 moves in the length direction of the microplate 300 and performs the detection of whether foreign matter is present on all the wells 310 in the next row (row 2) from the one end to the other end. This sequence is iterated to perform the detection of whether foreign matter is present on the wells 310 from the one end to the other end in all the rows in the length direction in the microplate 300, thereby carrying out the detection of whether foreign matter is present on all the wells 310 in the microplate 300.

Figure 7D:
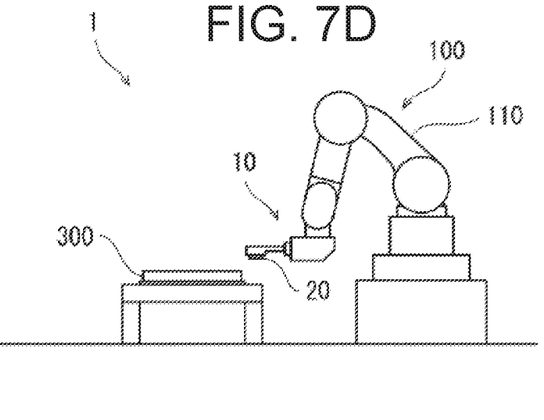

When the detection of whether foreign matter is present is carried out on all the wells 310 in the microplate 300, the detection of whether foreign matter is present in the wells 310 is completed. When the detection of whether foreign matter is present in all the wells 310 to be subjected to detection is completed, the hand section 10 is moved under control of the driving of the robot arm 110, and thereby the foreign matter detecting unit 20 is moved away from the microplate 300 as illustrated in FIG. 7D. Thus, the flow of the detection of whether foreign matter is present comes to an end.

In the present embodiment, the laser beam emitted from the light emitter is emitted to the center of a well 310 to be subjected to detection. Accordingly, the light axis L usually passes through a location near the diameter center at the entrance of the well 310 to be subjected to detection. For this reason, even if small foreign matter adheres to the side surface of a well 310 to be subjected to detection, the light may possibly pass without the light axis L blocked by the foreign matter. As a result, there may be considered a case where, even if foreign matter is present inside a well 310, the light axis L is not blocked and the distance between the foreign matter detecting unit 20 and the liquid surface of the blood in the groove 320 on the bottom surface of the well 310 is outputted, with the result that the absence of the foreign matter is determined. However, such small foreign matter is highly possibly removed already in the washing step prior to the foreign matter detection step.

In the present embodiment, the detection of whether foreign matter is present is performed for the purpose of detecting foreign matter which is relatively too large to be removed in the washing step. When foreign matter relatively too large to be removed in the washing step is present in a well 310 as illustrated in FIG. 6, the blood 410 is likely to remain below the foreign matter because the foreign matter is left occluding the well 310 due to a failure to remove the foreign matter from the well 310. A situation where not only the inside of the groove 320 on the bottom surface of the well 310 but also the inside of the well 310 below the foreign matter is filled with the blood 410 may affect a result of a test or analysis conducted subsequently on the blood.

In view of an influence on a result of a test or analysis conducted subsequently on the blood, the present embodiment has only to remove relatively large foreign matter that may prevent blood other than blood stored inside the groove 320 on the bottom surface of the well 310 from being removed in the washing step. To put it differently, what has to be done is only to detect relatively large foreign matter that, in the washing step, has occluded the well 310 and prevented the blood from being discharged from the well 310. This means to detect such relatively large foreign matter that a change in the position of the liquid surface of the blood can be detected as a result of a condition where the foreign matter occludes the well 310 and leaves the blood filling in the well 310 below the foreign matter.

The dispensing apparatus 1 of the present embodiment is capable of detecting whether foreign matter is present in each well 310 to be subjected to detection only by the foreign matter detecting unit 20 measuring the distance based on information on light from the well 310, and therefore a configuration for detecting whether foreign matter is present can be simplified.

The configuration for detecting whether foreign matter is present can be simplified in particular due to the unnecessity of both a mechanism for capturing an image of a sample and a high-performance analysis mechanism for obtaining various parameters from the image obtained by image-capturing of the sample. Accordingly, it is possible to keep low manufacturing costs for an apparatus that detects whether foreign matter is present in wells to be subjected to detection.

Moreover, according to the method of detecting foreign matter in the present embodiment, it is possible to detect whether foreign matter is present in each well 310 to be subjected to detection only by the foreign matter detecting unit 20 measuring the distance based on information on light from the well 310, and therefore the foreign matter detection can be performed in such simple method. This enables efficient foreign matter detection. The detection of whether foreign matter is present in each well 310 to be subjected to detection can be performed at high speed, and accordingly the detection of whether foreign matter is present in all the wells 310 to be subjected to detection can be completed within a short period of time.

Moreover, in the present embodiment, the hand section 10 in the main body 100 is configured to be capable of holding the foreign matter detecting unit 20 with the two finger parts 11 pinching the foreign matter detecting unit 20 in between. This configuration allows the hand section 10 to hold things other than the foreign matter detecting unit 20. For example, the hand section 10 can hold the microplate 300 with the two finger parts 11 pinching the microplate 300 in between. The main body 100 is capable of moving the microplate 300 by moving the robot arm 110 with the hand section 10 holding the microplate 300. Thus, the dispensing apparatus 1 may be configured such that: the detection of whether foreign matter is present in the wells 310 of the microplate 300 is performed with the hand section 10 holding the foreign matter detecting unit 20; and when the detection of whether foreign matter is present in all the wells 310 is completed, the hand section 10 releases the foreign matter detecting unit 20 from the holding and holds the microplate 300 instead, and the main body 100 moves the microplate 300 to a predetermined location. In addition, the hand section 10 can hold things other than the foreign matter detecting unit 20 and the microplate 300.

Although the foreign matter detecting unit 20 in the above embodiment is described such that the light emitter emits a laser beam and the light receiver receives the reflected laser beam, the disclosure should not be limited to the above embodiments. The light emitted from the light emitter in the foreign matter detecting unit 20 does not have to be a laser beam but may be any other type of light such as white light.

Moreover, in the above embodiment, the foreign matter detecting unit 20 measures the distance from the sample based on a phase difference between the phase of light emitted by the light emitter and the phase of light received by the light receiver. However, the disclosure should not be limited to the above embodiments. The distance may be measured in any other method, as long as the distance based on the information on the light from the well 310 can be measured.

Further, although the blood is used as a sample held in the wells of the microplate in the above embodiment, the disclosure should not be limited to the above embodiments. For example, other samples such as cerebrospinal fluid and urine may be used. Moreover, the sample may be one not used for the medical purpose, and any liquid sample may be used.

Furthermore, in the above embodiment, fibrin in the blood, a clot formed by blood coagulation, and the like are mentioned as foreign matter. However, the disclosure should not be limited to the above embodiments. When a sample other than blood is used, a substance produced by the sample may be treated as foreign matter. In addition, foreign matter may be one not produced by the sample. For example, foreign matter may be any matter not related to the sample, such as dust floating in the air.

Then, in the above embodiment, after the sample is dispensed into the wells 310 of the microplate 300 and the wells 310 are washed, the detection of whether foreign matter is present is performed on the wells 310. However, the disclosure should not be limited to the above embodiments. The detection of whether foreign matter is present may be performed on the wells 310 before the sample is dispensed into the wells 310. In this case, it is possible to detect whether foreign matter is present in the wells 310 into which the sample is yet to be injected. For example, there can be considered a case where dust or a mote may enter the inside of a well 310 before the sample is dispensed into the well 310. In such a case, the presence of the dust or mote can be detected. Then, the dust or mote can be removed from the well 310 before a sample is dispensed into the well 310. Since the detection of whether foreign matter is present can be performed on the wells 310 before the dispensing into the wells 310 as described above, a test or analysis on a sample can be performed to obtain a more accurate result of the test or analysis.

As described above, the determination step of determining whether foreign matter is present in the wells 310 may be performed before the dispensing step of dispensing a sample into the wells 310. Meanwhile, as in the present embodiment, the determination step of determining whether foreign matter is present in the wells 310 may be performed after the dispensing step of dispensing the sample into the wells 310 and the washing step of washing the insides of the wells 310.

The disclosure includes other embodiments in addition to the above-described embodiments without departing from the spirit of the disclosure. The embodiments are to be considered in all respects as illustrative, and not restrictive. The scope of the disclosure is indicated by the appended claims rather than by the foregoing description. Hence, all configurations including the meaning and range within equivalent arrangements of the claims are intended to be embraced in the description.

The invention claimed is:

1. A dispensing apparatus that dispenses a sample into a well of a microplate having a plurality of wells, comprising:
    a foreign matter detector comprising:
        a light emitter that emits light to each of the wells along a light axis; and
        a light receiver that receives light reflected from each of the wells or foreign matter in a least one of the wells and returning along the light axis, wherein the foreign matter detector outputs a distance from the wells or the foreign matter, the foreign matter remaining in the at least one of the wells after the plurality of wells have been washed so as to remove the samples from the plurality of wells;
    a multi-joint robot arm including a hand section configured to be capable of holding both the light emitter and the light receiver; and
    a control unit that determines whether the foreign matter is present in each of the wells based on the distance outputted from the foreign matter detector.

2. The dispensing apparatus according to claim 1, wherein the foreign matter detector measures a respective distance from the light receiver to the foreign matter if present, or the sample if the foreign matter is absent, in each of the wells.

3. The dispensing apparatus according to claim 2, wherein the foreign matter detector measures the respective distance from the light receiver to the foreign matter if present, or the sample if the foreign matter is absent, in each of the wells based on a phase difference between a phase of light emitted by the light emitter and a phase of light received by the light receiver.

4. The dispensing apparatus according to claim 3, wherein the light emitted by the light emitter is a laser beam.

5. The dispensing apparatus according to claim 2, wherein a threshold for the distance measured by the foreign matter detecting unit is set, and
    the control unit determines that foreign matter is present in each of the wells in response to the respective distance measured by the foreign matter detector being smaller than the threshold.

6. The dispensing apparatus according to claim 2, wherein the foreign matter detector is configured to be capable of being held by the hand section.

7. A dispensing method of dispensing a sample into a well in a microplate having a plurality of wells, comprising:
    dispensing the sample into the plurality of the wells;
    washing the plurality of wells so as to remove the dispensed sample from the plurality of the wells;
    emitting light to the plurality of the wells along a light axis;
    receiving light reflected from the plurality of the wells or foreign matter in a least one of the wells along the light axis, the foreign matter remaining in the at least one of the wells after the plurality of wells have been washed;
    outputting a distance from the wells or the foreign matter; and
    determining whether foreign matter is present in the plurality of the wells based on the outputted distance.

* * * * *